(12) United States Patent
Korobow

(10) Patent No.: US 6,224,564 B1
(45) Date of Patent: May 1, 2001

(54) ELASTIC ELBOW BRACE

(76) Inventor: Leon Korobow, 50 Cambridge Rd., Great Neck, NY (US) 11023

( * ) Notice: Subject to any disclaimer, the term of this patent is extended or adjusted under 35 U.S.C. 154(b) by 0 days.

(21) Appl. No.: 09/092,228

(22) Filed: Jun. 5, 1998

(51) Int. Cl.[7] .............................. A61F 13/00; A61F 5/37
(52) U.S. Cl. ........................ 602/62; 602/63; 128/881
(58) Field of Search .................... 602/5, 12, 20, 602/60–63, 75, 64; 2/455, 464, 465; D24/189; 128/881; 473/213, 214, 62, 63, 276

(56) References Cited

U.S. PATENT DOCUMENTS

| | | | |
|---|---|---|---|
| 4,084,586 | * | 4/1978 | Hettick .................... 602/60 |
| 4,424,809 | * | 1/1984 | Yovankin ................ 602/62 |
| 4,961,418 | * | 10/1990 | McLavrin-Smith ...... 602/21 |
| 5,069,203 | * | 12/1991 | Anderson ................ 602/21 |
| 5,449,341 | * | 9/1995 | Harris ...................... 602/63 |
| 5,591,121 | * | 1/1997 | Cantrell ................... 602/5 |
| 5,983,391 | * | 11/1999 | Palmer et al. ........... 2/16 |

FOREIGN PATENT DOCUMENTS

| | | | |
|---|---|---|---|
| 2632706 | * | 1/1978 | (DE) ........................ 602/63 |
| 510593 | * | 10/1992 | (EP) ......................... 602/20 |
| 2636229 | * | 3/1990 | (FR) ........................ 602/20 |

* cited by examiner

Primary Examiner—Mickey Yu
Assistant Examiner—Denise Pothier
(74) Attorney, Agent, or Firm—Bauer & Schaffer, LLP

(57) ABSTRACT

An elastic elbow brace for the prevention and treatment of tennis elbow, the brace having an elastic outer sleeve and a concentric inner sleeve. Interposed between the concentric sleeves is a pair of longitudinally extending resilient pads arranged parallel to each other and spaced along their longitudinal edges.

7 Claims, 2 Drawing Sheets

ELASTIC ELBOW BRACE

BACKGROUND OF THE INVENTION

The present invention relates to an elastic brace for tendons, elbows and similar body joints, and, in particular, to an elbow brace for preventing the development of tennis elbow and aiding in the relief of tennis elbow, should that have already occurred.

"Tennis elbow" as it is commonly known, is the inflammation of the elbow joint and the surrounding tendons caused by the repetitive swinging of a tennis racket and the shock exerted upon the elbow when striking the ball. The condition interferes with the player's enjoyment of the game; if left untreated can be quite painful, and ultimately result a disabling injury to the arm.

Numerous braces, pads and similar devices are currently available to reduce the shock of striking a ball. These devices are touted as aiding in the relief of, and/or preventing tennis elbow. These products, however, have not achieved widespread commercial success. The products referred to above generally fall within two groups, the first being generally ineffective, and the second although effective in relieving and/or preventing pain being so cumbersome as to hinder the player in playing the game.

It is therefore an object of the present invention to overcome the shortcomings and deficiencies found in the prior art.

It is a further object of the present invention to provide a elastic elbow brace that is effective in preventing and/or aiding in the relief of tennis elbow.

It is another object of the present invention to provide an elastic elbow brace that achieves the above objectives without hindering the player's performance.

These objects, together with other objects and advantages, will be apparent from the following disclosure of the present invention.

SUMMARY OF THE INVENTION

In accordance with the present invention, an elastic elbow brace having an elastic outer sleeve and a concentric inner sleeve between which is interposed two or more cushioning pads all assembled so as to apply a desired pressure on the arm in the vicinity of the elbow.

Full details of the present invention are set forth in the following description and illustrated in the accompanying drawings.

DETAILED DESCRIPTION OF THE INVENTION

Figure 1:
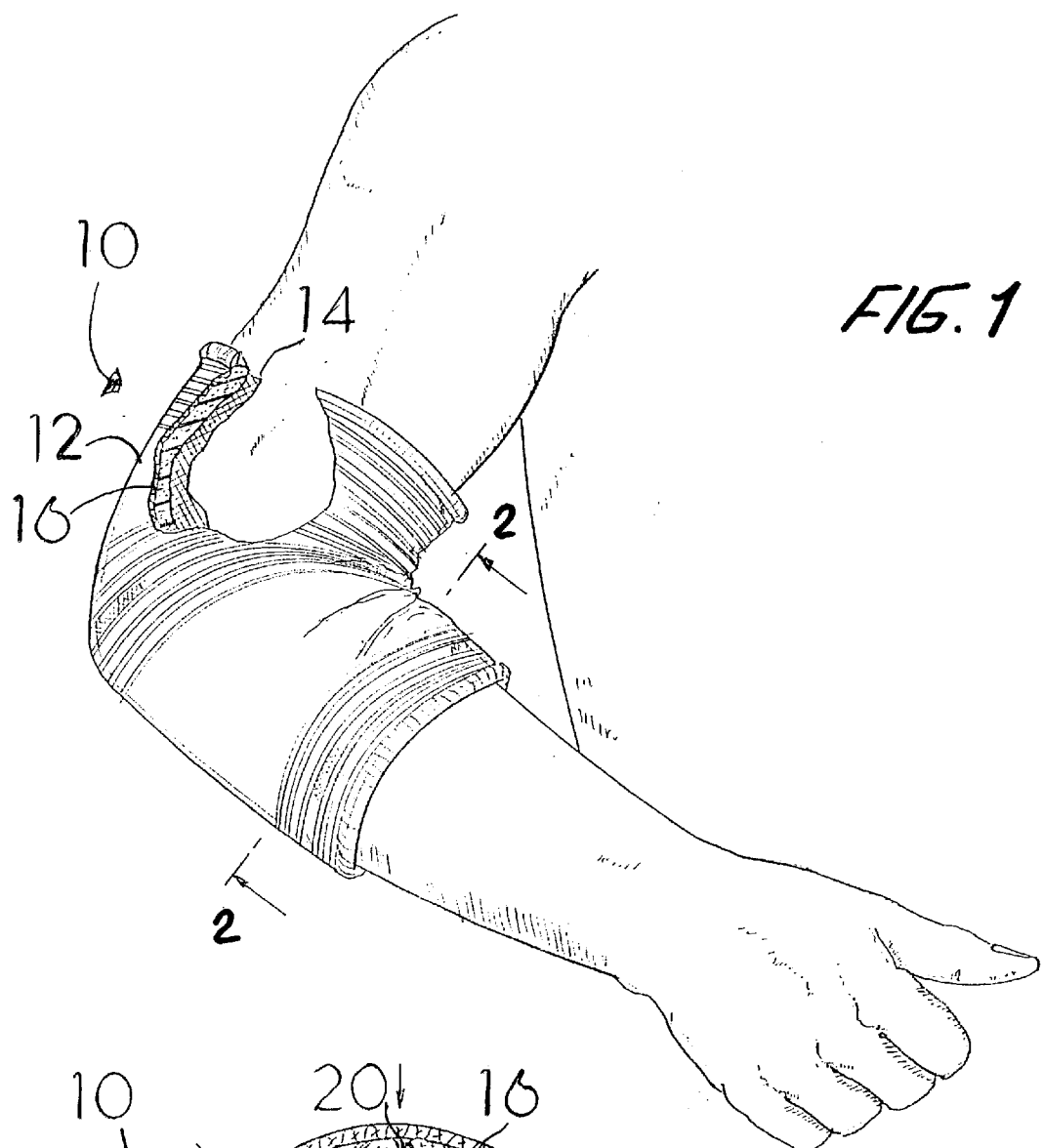
FIG. 1 is a perspective view of the elbow pad according to the present invention.
Figure 2:
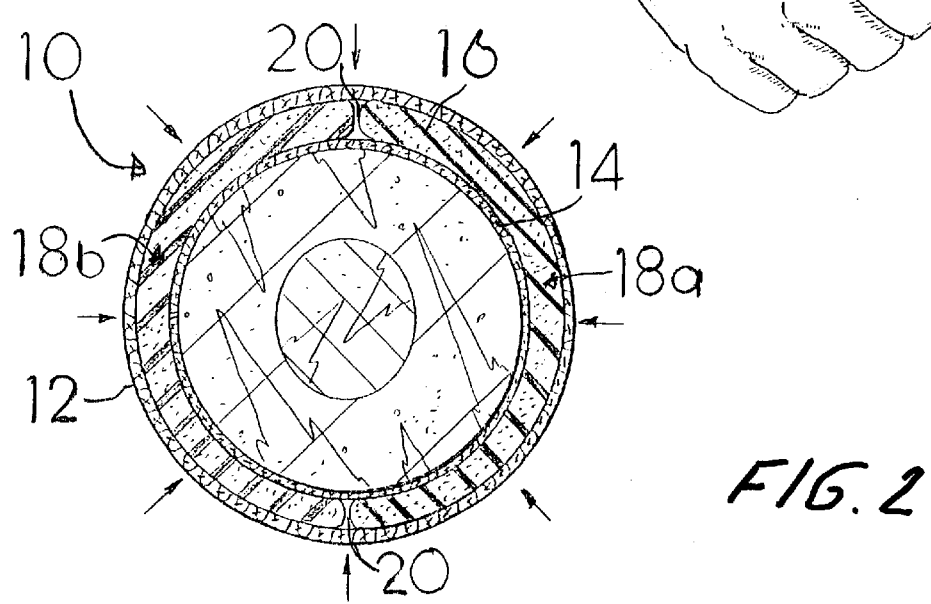
FIG. 2 is a sectional view taken along line 2—2 of FIG. 1, without the arm structure.

As seen in the Figures, the elastic elbow pad according to the present invention, generally depicted by the numeral 10, comprises a outer sleeve 12, an inner sleeve 14 and a intermediate pad construction 16 interposed therebetween. The sleeves 12 and 14 are coaxially arranged so that one overlies the next and are provided with a first and second open end so that the user can insert his arm through the first end and then through the second end pulling the two sleeves into the elbow position as shown in FIG. 1.

The outer sleeve 12 is constructed from a predominately radially elastic woven fabric (similar to an Ace bandage) that will flex with the movement of the elbow. The outer sleeve 12 gives the brace its overall functional shape while at the same time providing the requisite strength, positional stability and radial pressure with respect to the elbow.

The inner sleeve 14 is preferable constructed from a gauze like hypoallgenic woven fabric of minimal radial constriction that will act to provide a comfortable interface with the arm of the user while at the same time acting to absorb any perspiration. The inner sleeve 14 is preferably a thinner material than the outer sleeve.

The pad construction 16 is formed of two distinct generally non-elastic resilient pads 18a and 18b interposed between the inner and outer sleeves. The pads 18a and 18b are sandwiched between the inner and outer sleeves 12 and 14 so as to assume a generally semi-circular shape, the longitudinal edges of the pads lying in opposition to each other.

When the brace is in the unused or rest condition a small space 20 separates the longitudinal edges of the pads 18a and 18b so that the edges are in an almost abutting position. The pads 18a and 18b are preferable constructed from a polyester sponge material or foam plastic giving the brace the desired dampening properties. The pads may be anywhere from approximately ¼" to ½" in thickness depending on the flexibility desired.

Preferably the pads must have a degree of hardness that enables pressure to be sustained against the elbow but not so hard that the flexibility of the brace is reduced to a degree where arm movement is compromised. Thus it is contemplated that the harness of the pad will be selected for maximum benefit as dictated by the degree to which the user has been inflicted with "tennis elbow".

While only two pads 18a and 18b have been illustrated and found generally advantageous, it may be desirable to increase the number of pads each arranged parallel in the longitudinal direction.

Figure 3:
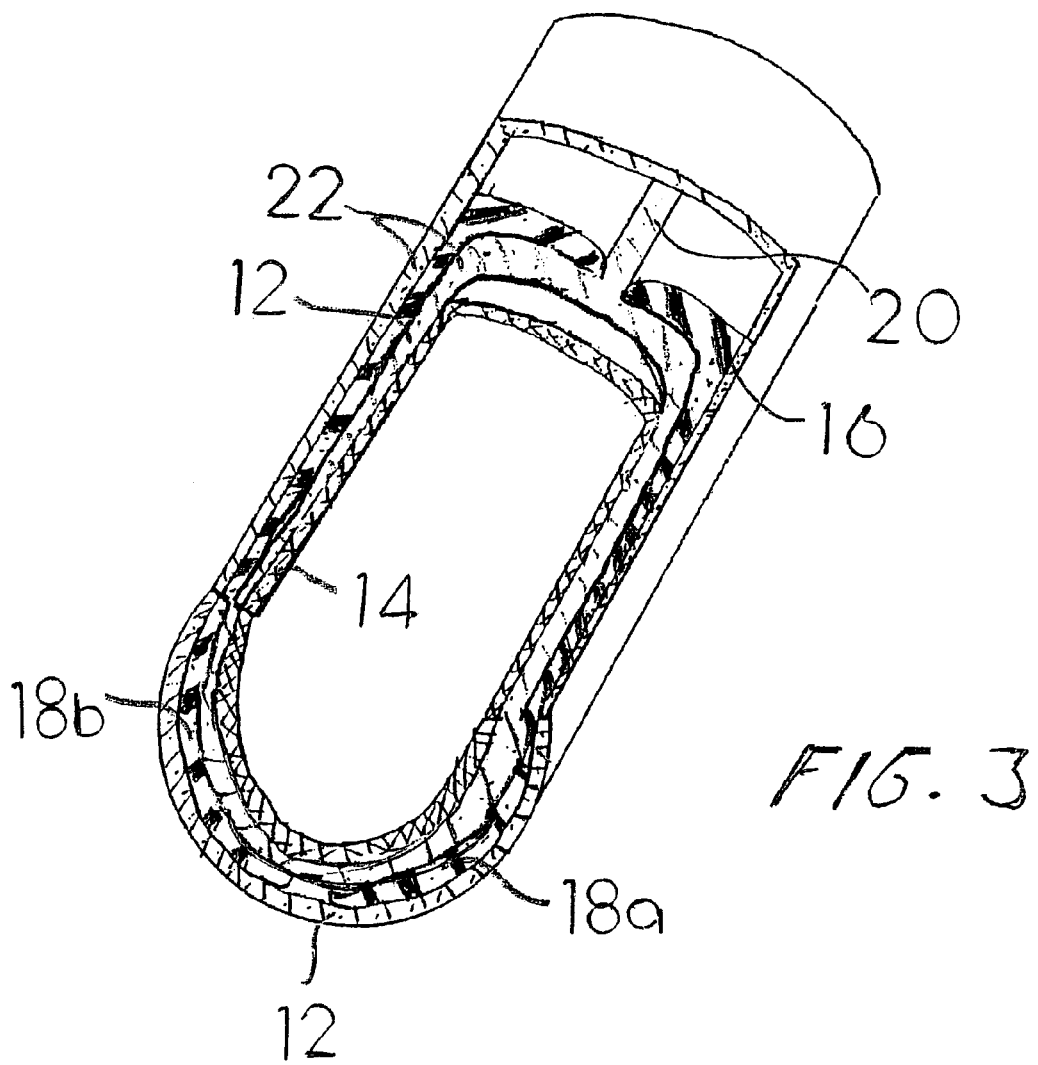
FIG. 3 is an isometric view of the elbow pad shown in FIG. 1, partially sectioned.

In assembly of the elastic elbow brace pads 18a and 18b may be securely fixed between the outer and inner sleeves if a permanent assembly is desired by sewing, glueing or otherwise securing the pads. Preferably one of the sleeves is formed with a pocket 22, as seen in FIG. 3, into which the pads are inserted. In this manner the brace can be disassembled and washed or otherwise cleansed.

As is customary the ends of the elbow brace may be hemmed or otherwise finished as would any conventional fabric device. Similarly the outer surface of the outer sleeve 14 may be colored or otherwise decorated.

In use, the user pushes his hand and arm through the elbow brace until the brace is positioned around the elbow. Because the brace is radially elastic, it stretches during insertion of the arm so that the pads interposed between the sleeves distend and separate. The brace is configured so that in use one pad runs along the outside surface of the arm while the other pad is placed along the inner side of the elbow from bicep to forearm.

The combination of radial pressure from the outer sleeve and the distending of the pads creates the desired force on the elbow preventing any damage or injury to the elbow. However, because of the space between the pads free movement of the elbow is preserved not withstanding the force placed on the elbow.

As will be seen from the foregoing the present invention provides an elbow brace for preventing and/or aiding in the relief of tennis elbow. The brace is effective in preventing injury to the elbow joint and the surrounding tendon without interfering with the player's performance or enjoyment of the game. The brace functions to absorb the reaction force generated by the impact of the tennis ball on the racket. The absorption occurs uniformly around the entire elbow without the brace unduly tightening or restricting the muscles, tendons or ligaments. The elbow thus heals quicker and more efficiently.

Various modifications have been suggested herein. Other changes and modifications will be apparent to those skilled in this art. It is therefore intended that the present disclosure be taken as illustrative only and not as limiting of the present invention.

What is claimed is:

1. An elastic elbow brace comprising an elastic outer sleeve, and an elastic inner sleeve forming a single channel and an intermediate pad construction comprising at least two uniformly thick resilient cylindrical sectors arranged within said channel between said sleeves and substantially colinear with said inner and outer sleeves, said pads having elongated longitudinal edges nearly abutting each other when said brace is not in use and spaced from each other on expansion of said sleeves when the user's arm is inserted therein maintaining the brace as a cylindrical structure.

2. The elastic elbow brace according to claim 1, wherein said pads are securely fastened between said inner and outer sleeves.

3. The elastic elbow brace according to claim 1, wherein one of said sleeves is formed with a pocket for the insertion of said pads, whereby said pads may be selectively inserted and removed from said brace.

4. The elastic elbow brace according to claim 3, wherein said outer sleeve is constructed from an elastic woven fabric.

5. The elastic elbow brace according to claim 4, wherein said inner sleeve is constructed from a hypoallergenic woven fabric.

6. The elastic elbow brace according to claim 5, wherein said pads are in the range of a ¼" to a ½" in thickness.

7. The elastic elbow brace according to claim 6, wherein said pads are constructed from a foam plastic.

* * * * *